United States Patent [19]
Sklar et al.

[11] Patent Number: 5,895,764
[45] Date of Patent: Apr. 20, 1999

[54] CONTROLLED SHEATH FLOW INJECTION CYTOMETRY

[75] Inventors: Larry A. Sklar, Albuquerque, N.M.; Larry C. Seamer, Pinole, Calif.

[73] Assignee: University of New Mexico, Albuquerque, N.M.

[21] Appl. No.: 08/976,637

[22] Filed: Nov. 24, 1997

[51] Int. Cl.$^6$ ................................. G01N 33/48
[52] U.S. Cl. ..................... 436/63; 436/52; 436/53; 436/164; 436/172; 356/317
[58] Field of Search ................. 436/52, 53, 63, 436/164, 172; 356/317, 338; 422/81, 82, 82.05, 82.08

[56] References Cited

U.S. PATENT DOCUMENTS

| | | | |
|---|---|---|---|
| 4,503,385 | 3/1985 | Haynes | 324/71.4 |
| 4,695,431 | 9/1987 | Farrell | 422/81 |
| 5,173,740 | 12/1992 | Fukuda et al. | 356/246 |
| 5,245,318 | 9/1993 | Tohge et al. | 340/611 |
| 5,395,588 | 3/1995 | North, Jr. et al. | 422/81 |
| 5,679,575 | 10/1997 | Kubota et al. | 436/49 |

FOREIGN PATENT DOCUMENTS

| | | |
|---|---|---|
| 0046345 | 2/1982 | European Pat. Off. |
| 06194299 | 7/1994 | Japan |

OTHER PUBLICATIONS

Hodder et al. *Analyst*, vol. 122, pp. 883–887, Sep. 1997.
Nolan, John P. et al., "Mix Flow Cytomer With Subsecond Kinetic Resolution", 1995, pp. 223–229, *Cytometer*.
Nolan, John P. et al., "Mix Flow Cytometer With Subsecond Kinetic Resolution", 1995, pp 223–229, *Cytometry*.

Primary Examiner—Maureen M. Wallenhorst
Attorney, Agent, or Firm—Hoffman, Wasson & Gitler

[57] ABSTRACT

A flow cytometry method and system to regulate both the sheath and sample streams during the period of sample injection. The period of turbulence between the streams is reduced to approximately 100 milliseconds thereby allowing for focused measurement of cell associated fluorescence.

7 Claims, 7 Drawing Sheets

CONTROLLED SHEATH FLOW INJECTION CYTOMETRY

BACKGROUND OF THE INVENTION

The invention relates to flow cytometers which are valuable tools for mechanistic studies of molecular interactions, such as cell function.

Flow cytometry allows particle associated fluorescence to be measured in comparison to fluorescence from the surrounding media which contributes very little to the measured signal. Cell associated fluorescence can be measured in a background of free fluorescent indicator. This is a valuable feature when determining ligand or dissociation kinetics where the cells must exist in a fluorescent milieu during analysis. In addition, flow cytometry allows for the examination of individual cells for kinetic analysis of selected populations in an heterogeneous mixture of cells. Bulk technologies such as fluorometry measure population average fluorescence and do not always distinguish free from bound fluorescence.

Early time measurements in conventional flow cytometers are limited by the time required to remove the sample tube from the instrument, inject reagent, manually mix the components return the sample tube and re-establish flow. This sequence usually requires a minimum of 7–10 seconds. Because of this limitation, the use of flow cytometry in the acquisition of kinetic data has been limited to processes with relatively slow kinetics. Many of the biological and biophysical processes of interest occur in less than five seconds. For example, in the study of receptor-ligand interactions, ligand binding affinity is calculated in part by determining the disassociation kinetics of the ligand. When the Kd of binding is in the microM range, off rates are sufficiently fast that they often cannot be measured by traditional flow cytometry.

Previously, sample handling systems designed to shorten this delay, have been explored (see FIGS. 1 and 2). These systems can be broadly classified into two groups: "time-window" and "time-zero" devices. Time-window systems continually analyze cells at a single time point after reagent mixing. To achieve a kinetic sequence, many individual measurements must be made, adjusting the sample delivery apparatus between measurements. The first such system was built around a simple mixing "T". The sample was injected from one side of the "T" and reagent from the other. Both sample and reagent were delivered at a constant slow rate, which together provided sample to the flow cell at a rate slow enough to allow stable laminar flow. The time point being measured was a function of the distance between the "T" and the laser interrogation point. Another approach using coaxial mixing has recently been reported. Coaxial mixing is a system in which sample is injected into the middle of a flowing stream of reagent. Once again, the time point measured is a function of the distance of the sample insertion tube from the laser interrogation point. These systems are useful when collecting large amounts of data at a single time point. However, they suffer when attempting to analyze a dynamic sequence of events.

Time-zero devices, on the other hand, mix sample and reagent at a single time point and follow the sequence of events over time. A stir-bar based sample mixing and injection system has been used by several groups. Stir-bar based systems employ a sample tube containing the cell suspension. Reagent is injected into the tube, mixed with a magnetic stir-bar and pushed to the flow cytometer laser interrogation point. Although one-second delivery times have been reported, it remains to be demonstrated that cells and reagent can be thoroughly mixed before arrival at the laser interrogation point. Mixing is more difficult in these systems because of the relatively large volumes used.

More recently, a syringe driven system has been described, in a published article, that has been shown to thoroughly mix small volumes in a reaction "T" and deliver the mixed sample to the laser in 300 mSec ("Rapid Mix Flow Cytometry with Subsecond Kinetic Resolution", Nolan et al., *Cytometry* 21, pp. 223–229, 1995.) Two features of this system significantly enhanced its ability to acquire data at very early time points. First, a valve is positioned proximal to the flow-cell sample input port. This allowed large volumes of mixed sample to be pushed quickly to that valve while shunting the excess volume to waste. The valve port is then changed directing the mixed sample to the flow cell at a much slower rate, easily accommodated by the flow cell orifice. Second, stable fluorescence measurements were improved by eliminating events that did not flow through the laser focal point by gating only on those events with an optimal forward light scatter signal. As seen in FIG. 2, cells not flowing through the center of the laser will receive less illumination, because of the gaussian intensity profile of a focused laser and because of the shorter distance across the beam when off-center. Therefore, cells forced outside the center of the laser beam by turbulent flow will have both a reduced light scatter signal as well as reduced fluorescence.

It is an object of the present invention to produce a syringe driven system without the interference of turbulent flow.

It is a further object of the present invention to provide an automated sample delivery system yielding maximum flexibility to accommodate a variety of applications.

It is a further object of the present invention to obtain particles in focus at the earliest time after the sample has been injected.

It is a further object of the present invention to control sheath flow in a flow cytometer to enhance and clarify particle analysis.

SUMMARY OF THE INVENTION

The invention provides computer controlled syringes to regulate and dispense both the sheath and sample streams of a flow cytometer during the period of sample injection. The period of turbulence of flows are reduced to less than 200 milliseconds. The shortened time frame to re-establish laminar flow is accomplished by controlling sheath flow. The mixed sample is moved at higher flow rates for 50 milliseconds after a valve has redirected the flow into the flowcell. To avoid overloading the flowcell's ability to accommodate the large volume, the sheath flow is suspended during that time. After 50 milliseconds, the sample flow rate is reduced to 2 µl/second and sheath flow is once again increased to 48 µl/second. This technique shortens the time to achieve stable flow in the system by at least a full second.

DETAILED DESCRIPTION OF THE PREFERRED EMBODIMENTS

Figure 1:
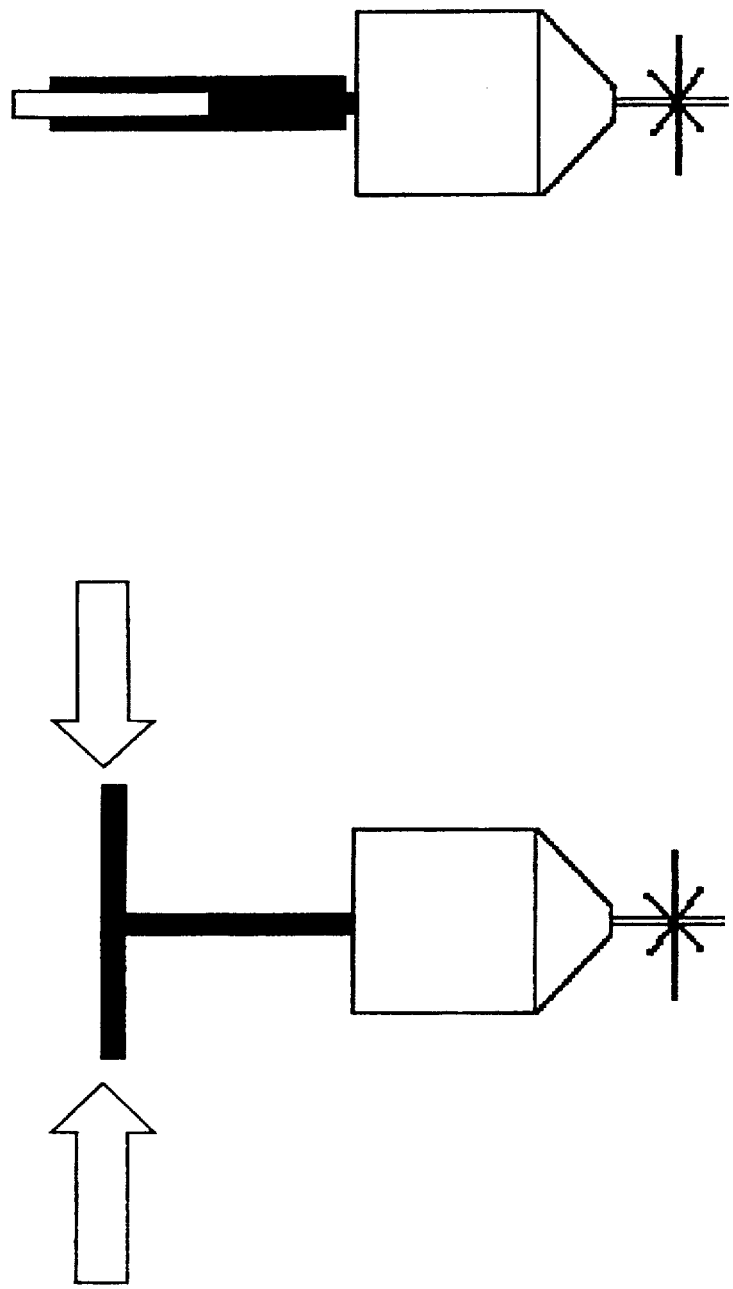
FIG. 1 illustrates time-window handling systems.
Figure 2:
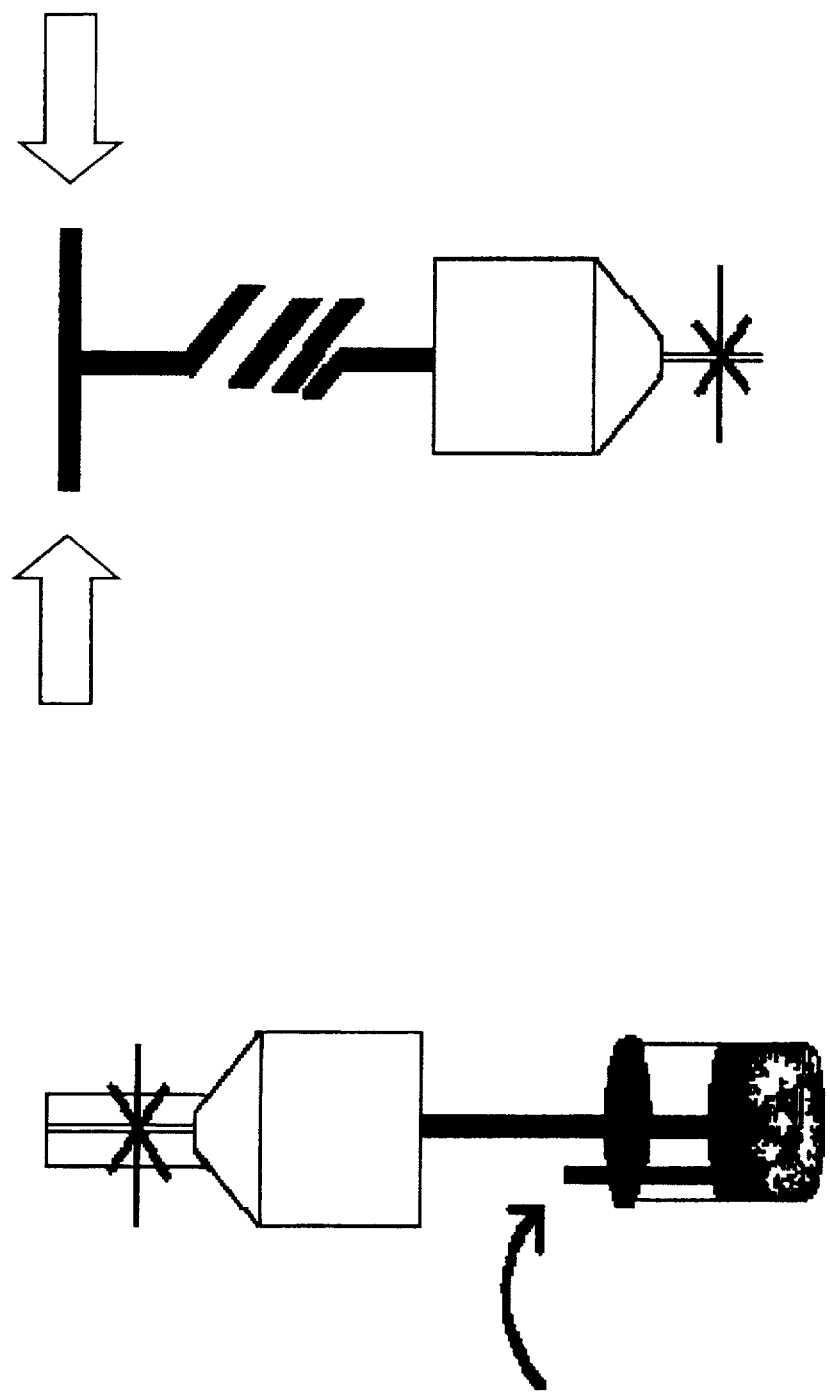
FIG. 2 illustrates time-zero handling systems.
Figure 3:
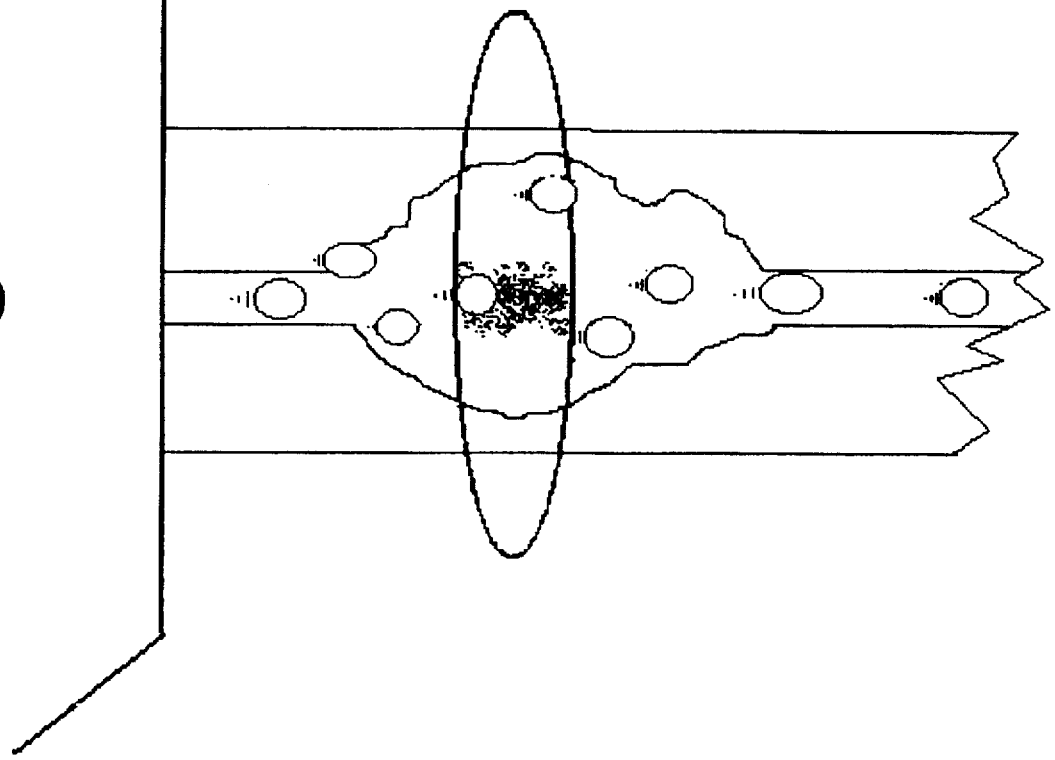
FIG. 3 is a depiction of turbulent flow in a flow cytometry tube upon interaction of sheath and sample in an existing cytomer.
Figure 4:
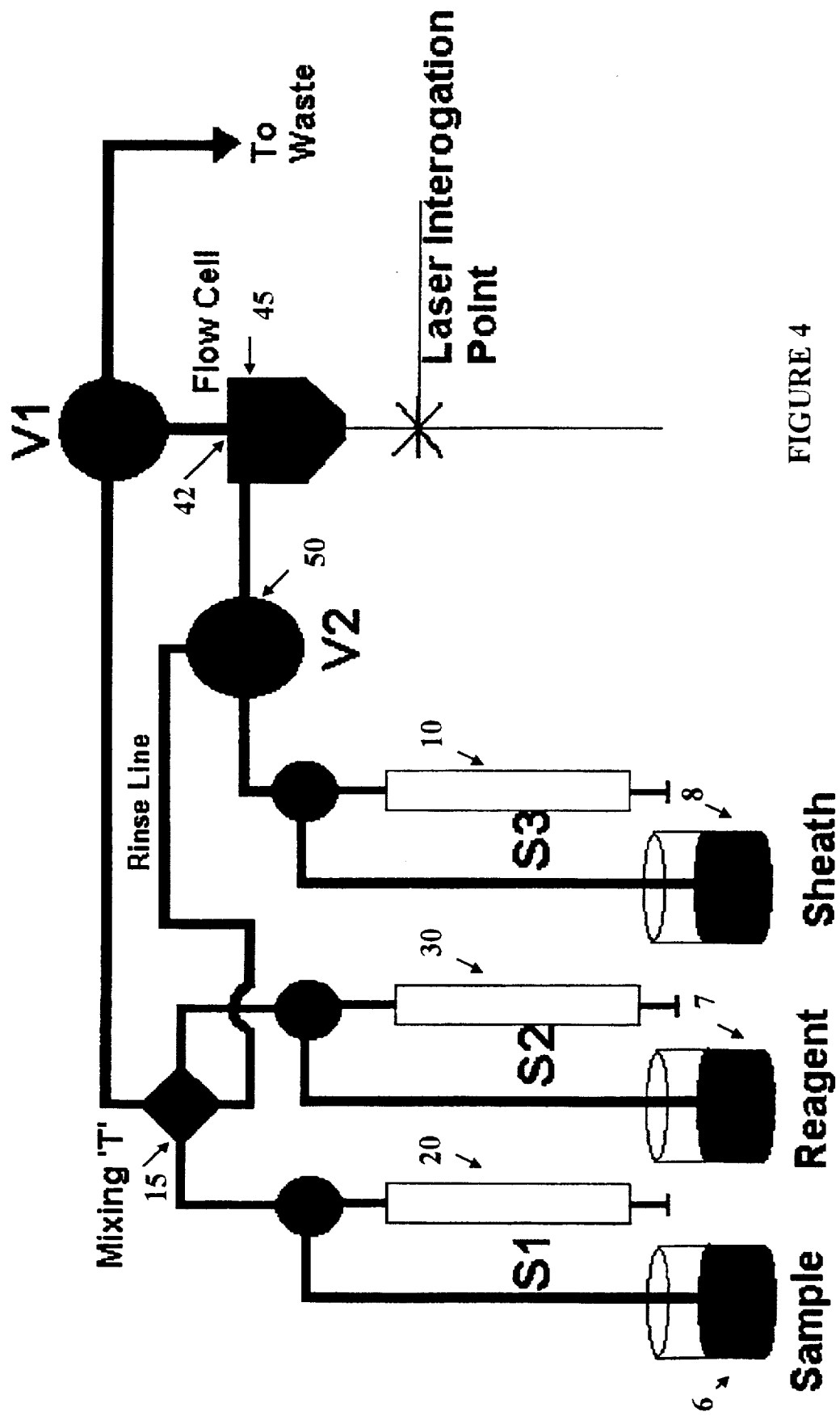
FIG. 4 illustrates the sample mix and injection system of the present invention.

FIG. 4 shows details of the sample mix and injection system used for this work. Numeral 10 designates a 5 ml syringe pump used to dispense sheath buffer. Numeral 20 designates a 1.0 or 0.5 ml syringe pump used to dispense sample (either cells or beads) to the mix line and then used to deliver the sample-reagent mixture to the flow cytometer. Numeral 30 designates a 1.0 or 0.5 ml syringe pump used to deliver reagent to the mix line. Valve 40 is a 6-position valve, positioned as close as possible to the flow cell 45 sample-input port 42, approximately 3 cm. Valve 50 is an identical valve used to direct the sheath buffer to the flow cell during normal operation, redirecting sheath to the mixing line, for rinsing between samples.

Reservoirs 6, 7 and 8, contain sample, reactant and sheath, respectively.

A typical sequence and timing of commands, as shown in Table 1, are as follows: Stable sheath flow is established 8 seconds prior to sample mixing. The next five commands are given in succession with no requested delay times, therefore, the time delay is limited only by the minimum time per command, described above. First, sheath flow is reduced to 2 μl/Sec. Second, reagent push is begun. The third and fourth commands create a time-mark. With the fifth-command sample and reagent mixing occurs, as sample flow is begun. The total dead-time is 75 milliseconds from creation of the time-mark to actual sample mixing. Sample and reagent push continue at 150 μl/sec total flow rate for 300 milliseconds. The mix line between the mixing valve 15 and the control valve 40 hold 45 μl. Therefore, mixed sample has been pushed past valve 40 during this 300 milliseconds. Next, valve 40 changes position, directing the mixed sample towards the flow cell 45. 50 milliseconds later, sample push is slowed to 2 μl/Sec, the stable analyses rate. Immediately, sheath flow is increased to 48 μl/Sec and stable laminar flow is re-established.

TABLE 1

| TIME/ mSec | (sample) μL/Sec | (reagent) μL/Sec | (sheath) μl/Sec | Valve 40 position | Time Pulse |
|---|---|---|---|---|---|
| −8,000 | 0 | 0 | 50 | Waste | Off |
| −100 | 0 | 0 | 2 | Waste | Off |
| −50 | 0 | 75 | 2 | Waste | Off |
| 0 | 0 | 75 | 2 | Waste | On |
| +25 | 0 | 75 | 2 | Waste | Off |
| +75 | 75 | 75 | 2 | Waste | Off |
| +375 | 75 | 75 | 2 | Flow Cell | Off |
| +425 | 2 | 75 | 2 | Flow Cell | Off |
| +475 | 2 | 75 | 48 | Flow Cell | Off |
| +525 | 2 | 0 | 48 | Flow Cell | Off |

A significant difference between this instrument and earlier rapid mix devices is that we now control sheath as well as sample and reagent delivery. One of the primary obstacles to sub second measurements by flow cytometry is the competing requirement to deliver relatively large volumes of mixed sample to the flow cell quickly and the necessity of retaining stable laminar flow. As in the previous instrument, most of the early push of sample is directed through the valve 40 to waste, allowing the sample to be brought close to the flow cell very rapidly. However, sample must then move the final distance, from valve 40 to the laser interrogation point, with minimal perturbations in flow. We reasoned that if sheath flow could be reduced for the 300 milliseconds that sample is quickly moved from valve 40 to the laser, while maintaining the same overall flow rate 50 μl/Sec, stable flow would more quickly re-establish when sheath and sample were returned to their appropriate flow rates (sheath=48 μl/sec, sample=2 μl/sec). To demonstrate the affect of sheath control, beads were run with the sheath rate reduced from its normal rate of 48 μl/sec to 2 μl/sec for 300 milliseconds while the mixed sample is redirected from waste to the flow cell. When the normal laminar flow is perturbed, some beads will not flow through the optimal laser focus point and will be measured with a reduced fluorescence. Therefore, by monitoring fluorescence intensity during the early time points stable flow can be quantified. These data were compared to data collected similarly, but, with sheath maintaining a constant 50 μl/sec flow rate throughout sample push.

Figure 5:
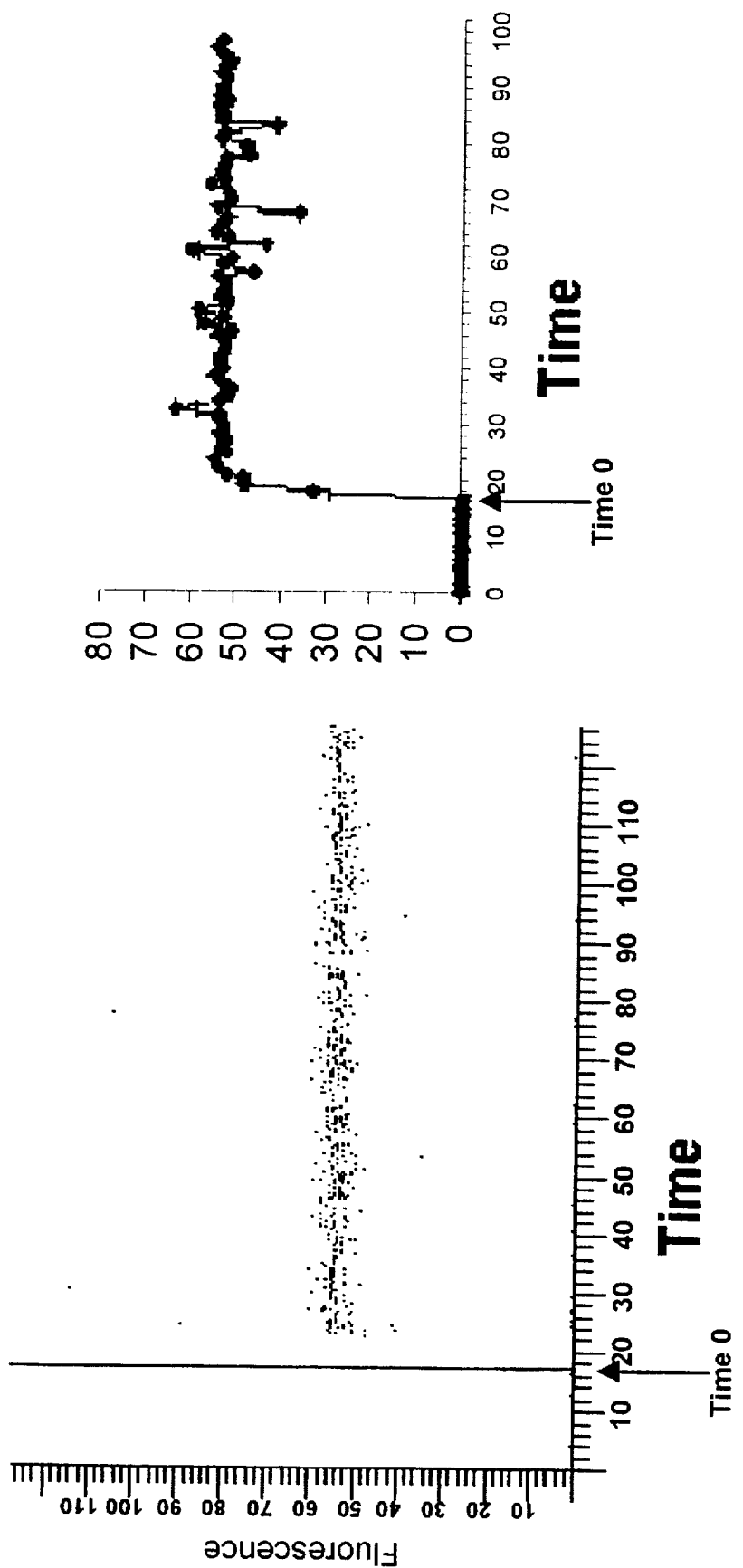
FIG. 5 shows a typical dot-plot of beads collected with sheath control comparing fluorescence versus time, in intervals of one hundred millisec.
Figure 6:
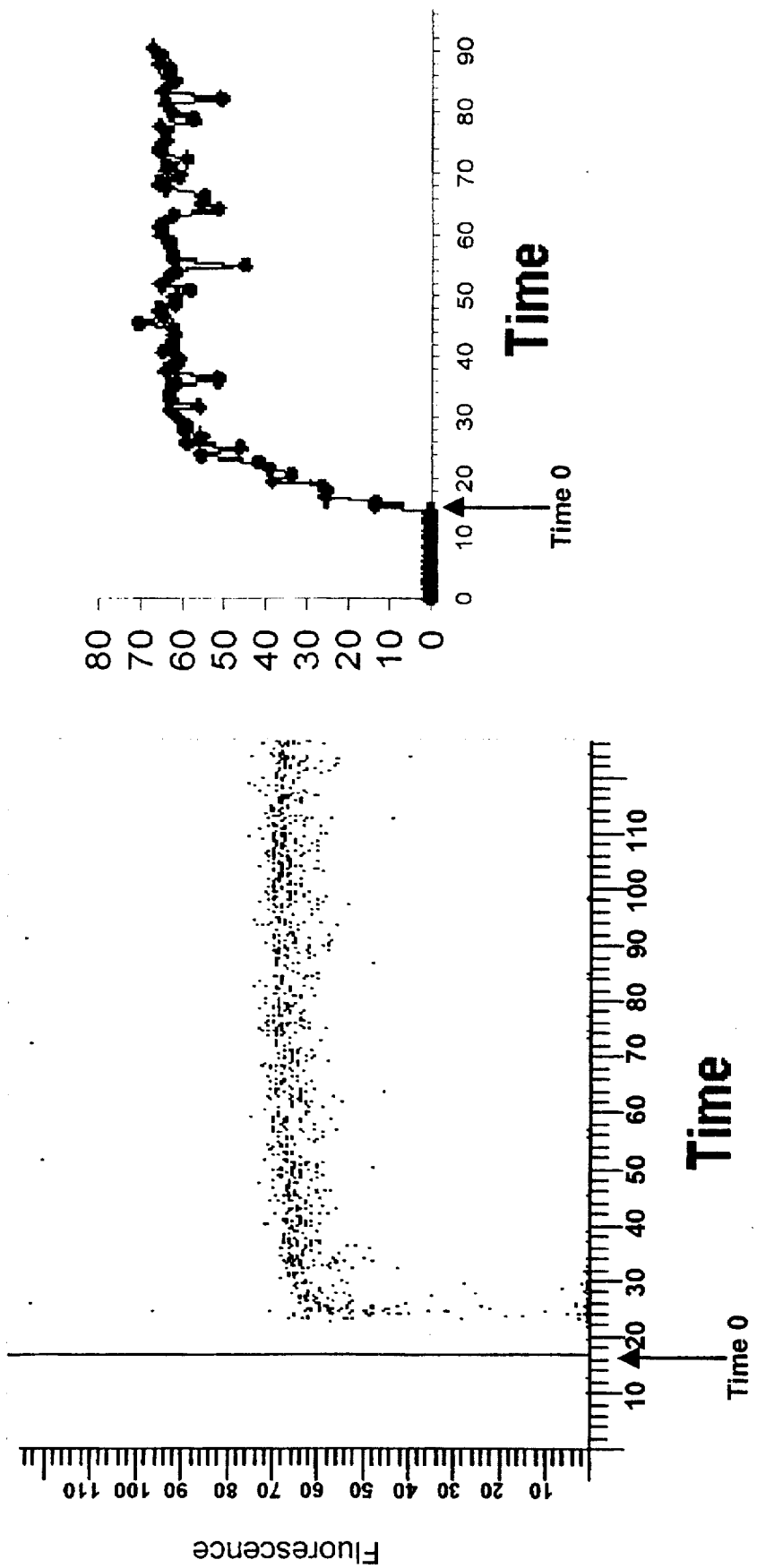
FIG. 6 shows a typical dot-plot of beads collected without sheath control comparing fluorescence versus time, in intervals of 10.0 millisec.
Figure 7:
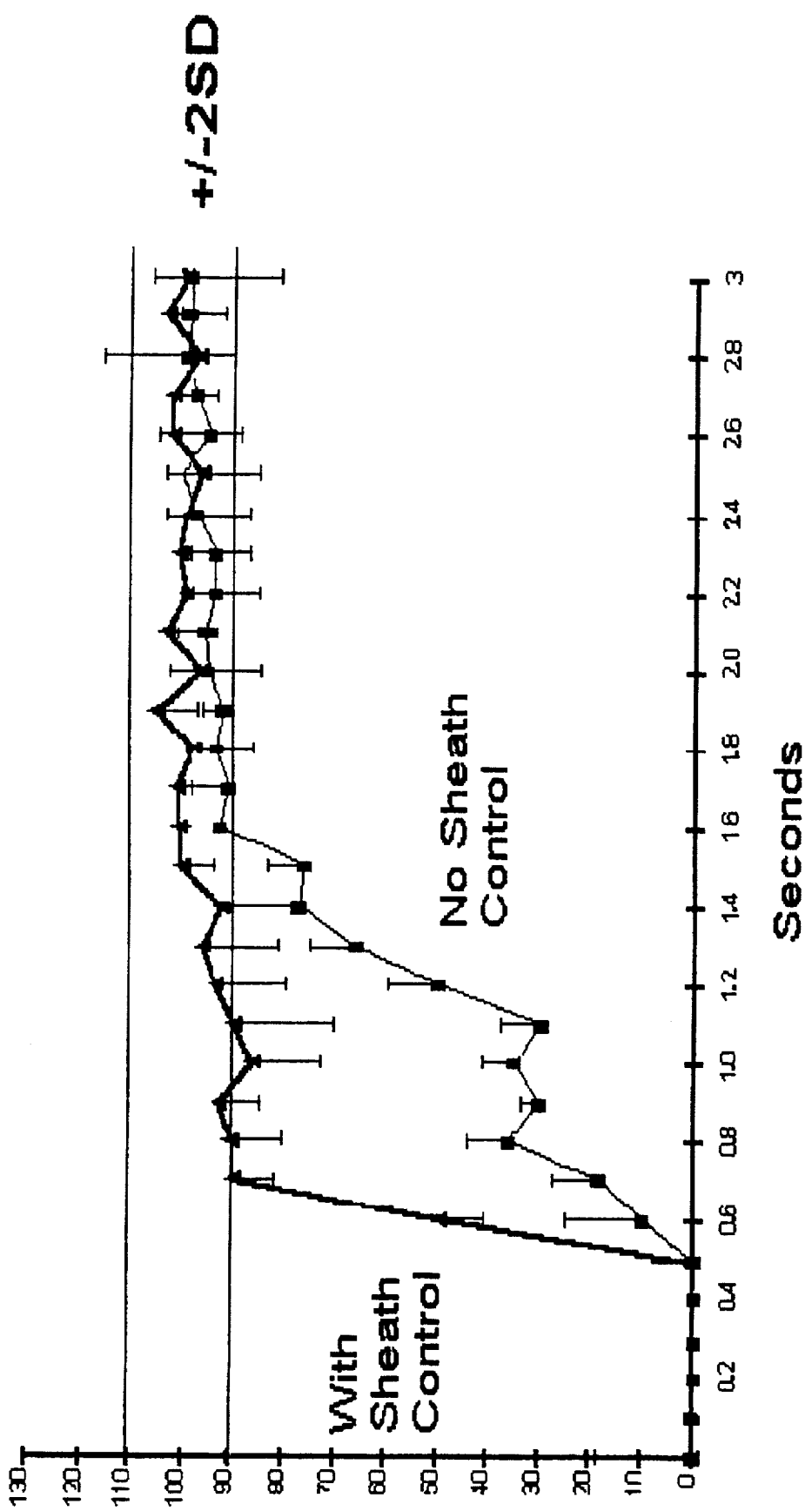
FIG. 7 shows a plot of the mean fluorescence for the average of five replicates, as in FIGS. 5 and 6, each with and without sheath flow reduction.

FIGS. 5 and 6 show a typical dot-plot of beads collected with and without sheath control. The calculated mean fluorescence line graph is shown next to each dot-plot. FIG. 7 shows the average mean-fluorescence of five replicates each with and without sheath flow reduction. This figure demonstrates that with sheath control, bead fluorescence reaches its maximum value±2 standard deviation, in 200 milliseconds after restoring sheath flow buffer. However, with no sheath reduction, stable fluorescence measurements were not achieved for 1 second, clearly showing the advantage of sheath control with this device.

The difficulty of rapid mix flow cytometry is primarily caused by the need to move relatively large volumes of cells and reagent to the laser interrogation point very quickly, while flowcells can accommodate very slow flow rates. The incorporation of a sample-line valve just above the flow cell allows us to mix and move the necessary volumes close to the flow cell before directing the sample towards the flow cell. However, the mixed sample must still be moved the final distance to the laser quickly while retaining or quickly re-establishing well behaved stable flow conditions. We have shortened the time needed to re-establish stable flow by controlling sheath flow. Specifically, we continue to push the mixed sample at higher flow rates for 50 milliseconds after the shunt valve has redirected the flow into the flowcell. To avoid overloading the flow cell's ability to accommodate the large volume, the sheath flow is suspended during that time. After 50 milliseconds, the sample flow rate is reduced to the more typical 2 μl/second and sheath flow is once again increased to 48 μl/sec. We have shown that this technique shortens the time to achieve stable flow in our system by at least a full second.

Possible applications of such an instrument include drug binding or competitive inhibition studies, cell signaling, cell physiology, cell morphometry and bead based assays. In this work we first verify instrument performance, insuring adequate mixing and stable sample delivery. The invention provides a significant improved modification of previous syringe based time-zero systems, showing that a stable flow can be re-established much more quickly than otherwise possible by reducing sheath delivery during the brief period of simple push.

What is claimed is:

1. A method for flow cytometry comprising the steps of:
    a) delivering a rapid sheath flow through a flow cell of a flow cytometer at an initial flow rate;

b) rapidly mixing a sample and a reactant outside said flow cell for delivery to said flow cell;

c) reducing flow of said sheath through said flow cell to a lower flow rate;

d) delivering mixed sample and reactant through said flow cell during the time when the flow of said sheath is reduced;

e) redelivering said rapid sheath flow through said flow cell at said initial flow rate; and f) measuring a cell fluorescence of said mixed sample and reactant; whereby focused measurement of said sample is obtained due to reduced turbulent flow of sheath, sample and reactant.

2. A method for flow cytometry as claimed in claim 1, wherein a means is provided for reducing flow of said sheath through said flow cell.

3. A method for flow cytometry as claimed in claim 2, wherein said means for reducing flow of the sheath is a valve or syringe.

4. A method for flow cytometry as claimed in claim 1, wherein a means is provided for mixing sample and reactant for delivery to said flow cell, said means is a valve or syringe.

5. A method for flow cytometry as claimed in claim 1, wherein a means is provided for regulating delivery of said mixed sample and reactant for delivery to said flow cell, said means is a valve or syringe.

6. A method for flow cytometry as claimed in claim 1, wherein delivery of said sheath flow and delivery and mixing of said sample and said reactant are accomplished by first, second and third syringes.

7. A method for flow cytometry as claimed in claim 1, wherein measurement of said cell fluorescence is accomplished by a laser.

* * * * *